United States Patent [19]
Schneider et al.

[11] Patent Number: 5,688,911
[45] Date of Patent: Nov. 18, 1997

[54] TRK NEUROTROPHIN BINDING MOTIFS

[76] Inventors: Rainer Schneider, Canisiusweg 125/4/34, A-6064 Rum; Jörg M. Windisch, Josef-Stapf-Strasse 1, A-6020 Innsbruck, both of Austria

[21] Appl. No.: 434,198

[22] Filed: May 3, 1995

[51] Int. Cl.$^6$ .............................. C07K 14/71; C07H 21/00
[52] U.S. Cl. .......................... 530/324; 536/23.1; 536/23.5
[58] Field of Search ................................. 536/23.1, 23.4, 536/23.5; 530/325, 387.3

[56] References Cited

PUBLICATIONS

Urfer et al., *EMBO J.*, vol. 14, pp. 2795–2805, 1995.

*Primary Examiner*—Donald E. Adams
*Assistant Examiner*—Stephen Gucker
*Attorney, Agent, or Firm*—Gail M. Kempler

[57] ABSTRACT

Trk neurotrophin binding motifs consisting of 24 amino acid, leucine rich domains are described as well as nucleic acid sequences encoding such peptides. The leucine rich motifs are useful in screens for novel agonists and antagonists of the neurotrophins.

6 Claims, No Drawings

TRK NEUROTROPHIN BINDING MOTIFS

BACKGROUND OF THE INVENTION

Brain-derived neurotrophic factor (BDNF); neurotrophin 3 (NT-3) and neurotrophin-4 (NT-4) are members of the growing family of neurotrophins, the paradigm of which is nerve growth factor (NGF). Neurotrophins are target-derived dimeric peptide hormones which play an important role in neuronal cell survival and differentiation (Thoenen 1991, Trends Neurosci. 14: 165–170; Raffioni, et al. 1991, Ann. Rev. Biochem. 62:823–850; Chao, 1992, Neuron 9:583–593; Barbacid 1993, Oncogene 8:2033–2042).

Neurotrophins bind to two discrete receptor types which can be distinguished pharmacologically. p75NGFR binds all known neurotrophins with similar nanomolar affinities (Rodriguez-Tebar, et al. 1990, Neuron 4:487–492; Barker and Murphy, 1992, Mol. Cell. Biochem. 110:1–15). Cells expressing TrkA, a tyrosine kinase receptor originally identified as a human oncogene (Maltin-Zanca, et al, Nature 319: 743–748) bind solely NGF and exhibit significantly slower dissociation kinetics (Jing, et al. 1992, Neurol. 9:1067–1079; Loeb and Greene, 1993, Neuroscience 13:2919–2929.

An increasing number of studies has revealed that among the neurotrophins especially BDNF, NT-3, and NT-4, the three ligands of the TrkB receptor tyrosine kinase (Glass et al 1991, Cell 66:405–413; Squinto et al. 1991, Cell 65:885–893; Klein et al., 1991, Cell 66:395–403; Klein et al. 1992, Neuron 8:947–956; Ip et al., 1993, Neuron 10:137–149; Soppet et al 1991, Cell 65:895–903), have great therapeutic potential in the treatment of neurological disorders and injuries (Lindsay et al 1994 Trends Neurosci. 17:182–190; Schnell et al 1994, Nature 367:170–173; Yan et al. 1992 Nature 360:753–755; Koliatsos et al. 1994, Proc. Natl. Acad. Sci U.S.A. 91:3304–3308; Mitsumoto et al 1994, Science 265:1107–1110; Ghosh et al. 1994, Science 263:1618–16;23).

The cDNA encoding the TrkB tyrosine kinase receptor was first cloned using a probe specific for the human protooncogene trk. The open reading frame encodes a protein approximately 800 amino acids in length with a calculated Mr of the polypeptide core of 92 kd. Studies using antibodies raised against carboxy-terminal sequences of TrkB revealed that the trkB gene product is a glycoprotein with an apparent molecular weight of 145 kd ($p145^{trkB}$), indicating that more than 50% of the mass of the extracellular domain are made up of carbohydrates TrkB was shown to be expressed mainly in the CNS, which gave a first clue that it may serve a function in the development and/or maintenance of the nervous system (Klein et al., 1989, EMBO J. 8:3701–3709; Hofer et al., 1990, EMBO J. 9:2459–2464).

Further studies on trkB expression in mouse (Klein et al, 1990, Cell 61:647–656) as well as rat (Middlemas, et al. 1991, Mol. Cell. Biol. 11:143–153) revealed the existence of truncated TrkB receptors ($gp95^{trkB}$) lacking most of the cytoplasmic kinase domain and showing some variation in their C-terminus. Rat TrkB has 37% amino acid sequence identity in the extracellular domain and 75% in the kinase domain with the product of the human protooncogene trk, the receptor tyrosine kinase TrkA (Middlemas et al. 1991 Mol. Cell. Biol. 11:143–153).

Pharmacologically, TrkB receptors are characterized by their slow dissociation kinetics with half lives >10 min (Schechter & Bothwell 1981, Cell 24:867–874; Meakin et al 1992, Proc. Natl. Acad. Sci. U.S.A. 89:2374–2378; Meakin & Shooter 1992, Trends Neurosci. 15:323–331; Rodriguez-Tebar & Barde 1988, J. Neuroscience 8:3337–3342,; Rodriguez-Tebar et al 1992, EMBO J. II:917–922) which earned TrkA the synonymous designation "slow NGF receptor". It is generally recognized that Trk receptors transduce most of the biologically relevant signals exerted by neurotrophins to the interior of the cell since the trophic activities of the individual neurotrophins correspond well with the expression of their cognate Trk receptors (Meakin & Shooter 1992, Trends Neurosci. 15:323–331; Lindsay et al 1994, Trends Neurosci. 17:182–190). The importance of TrkB receptors in ontogeny was impressively demonstrated by the targeted disruption of the trkB gene in mice which results in severe nervous system lesions and neonatal death (Klein et al 1993, Cell 75:113–122). Very little is known at this point about the interactions between TrkB and its ligands at the molecular level BDNF and NT-3 bind to non-neuronal cells ectopically expressing TrkB receptors with affinities in the range of 1 nM (Soppet et al., 1991, Cell 65:895–903; Glass et al. 1991, Cell 66:405–413; Dechant et al., 1993, Development 119:545–558). No detailed studies on the interactions between NT-4 and TrkB in terms of binding characteristics are yet available.

The so called low-affinity neurotrophin receptor ($p75^{LNTR}$) is more widely expressed than the Trk receptors and binds all know neurotrophins with similar low affinities in the nanomolar range albeit with distinct kinetics (Barbacid, 1993, Oncogene 8: 2033–2042) Pharmacologically $p75^{LNTR}$ displays characteristics distinctly different from the Trk receptors in that the off-rate is much faster ($t_{1/2}$~3s) (Meakin et al. 1992, Proc. Natl. Acad. Sci. U.S.A. 2374–2378). The roles of $p75^{LNTR}$ in the formation of a possible neurotrophin binding receptor complex and its function in signal transduction are still controversial. Recent studies, however, have indicated that Trk and $p75^{LNTR}$ indeed collaborate in the binding and signal transduction of neurotrophins (Verdi et al. 1994, Neuron 12:733–745; Barker & Shooter, 1994, Neuron 13:203–215; Hantzopoulos et al., 1994, Neuron 13:187–201).

The molecular mechanisms by which neurootrophins interact with their respective Trk receptors are poorly characterized. TrkB shares with TrkA and a third homologous receptor TrkC, which preferentially binds NT-3 (Lamballe, et al. 1991, Cell 66:967–979) a unique mosaic of distinct structural modules in the extracellular domain as identified by Schneider & Schweiger, 1991, Oncogene 6:1807–1811 using special sensitive sequence comparison algorithms. More specifically, there is an N-terminal LRM3-cassette and a Ig2-domain adjacent to the membrane. The $LRM_3$-cassette consists of two cysteine-rich clusters (containing a total of eight cysteine residues) which are separated by a tandem array of three leucine-rich motifs (LRMs). The Ig2-domain is made up of two immunoglobulin-like modules of the C2 type (Schneider & Schweiger, 1991, Oncogene 6:1807–1811).

LRM repeats are capable of exerting strong and specific protein-protein interactions. They have been found in proteins as diverse as human glycoprotein IX (Lopez et al., 1987, Proc. Natl. Acad. Sci. U.S.A. 84:5616–5619), Drosophila Toll (Keith & Gay 1990, EMBO J. 9:4299–4306) and Drosophila Chaoptin (Krantz & Zipurksy, 1990, EMBO J. 9:1969–1977), where they mediate cell-cell interactions and communication yeast adenylate cyclase, where they form the interaction site with the Ras protein (Suzuki et al., 1990, Proc. Natl. Acad. Sci. U.S.A. 87:8711–871 5), and human ribonuclease (angiogenin) inhibitor which consists almost entirely of LRMs and exerts one of the strongest protein-protein interactions known so far (Lee & Vallee 1993, Prog. Nucleic Acid Res. Mol. Biol. 44:1–30; Lee et al 1988, Biochemistry 27:8545–8553; Schneider et al., 1988, EMBO J. 7:4151–4156). An individual LRM contains around 22 to 30 amino acids with hydrophobic residues at conserved positions. LRMs are tandemly repeated in a distinct protein with the number of repeats ranging from a single LRM to as many as 30 (Schneider et al., 1988, EMBO J. 7:4151–4156; Schneider & Schweiger 1991, Oncogene 6: 1807–1811; Kobe & Deisenhofer 1994, Trends Biochem. Sci. 19:415–421).

On the other hand, immunoglobulin-like domains are firmly established as potent ligand binding domains. The keratinocyte growth factor receptor (Yayon, et al. 1992 EMBO J. 11:1885–1890), the macrophage colony stimulating factor receptor (Wang, et al. 1993 Mol. Cell. Biol. 13:5348–5359), and the intercellular adhesion molecule (ICAM-I) (Diamond, et al. 1991 Cell 65:961–971) are prominent examples of receptors that utilize Ig-like domains for ligand binding.

SUMMARY OF THE INVENTION

The object of the present invention is to provide peptides derived from the Trk family of tyrosine kinase receptors which constitute the neurotrophin binding regions of these receptors. Such peptides may be used as antagonists of neurotrophin activity, or may be utilized in screens to identify compounds capable of binding the region critical to neurotrophin/Trk receptor interaction, thereby acting as either antagonists or agonists of neurotrophin activity.

DETAILED DESCRIPTION OF THE INVENTION

The present invention is directed to peptide regions derived from the extracellular domains of Trk receptors that are useful for the identification of novel agonists and antagonists of neurotrophins. As used herein, members of the neurotrophin family include nerve growth factor (NGF), brain derived neurotrophic factor (BDNF), neurotrophin-3 (NT-3) and neurotrophin-4 (NT-4) as well as combinations or chimeras or heterodimers thereof. The present invention is based on applicants discovery that specific structures within the extracellular domain of the Trk receptors are critically involved in the binding of neurotrophins to these receptors.

As described herein, applicants have discovered that a single leucine rich domain within each of the Trk receptor extracellular domains is involved with binding of the neurotrophin to the receptor.

Applicants identification of the binding site(s) for NGF in TrkA, and the binding site(s) for BDNF, NT-3 and NT-4 in TrkB was accomplished by expressing the two major structural components of each Trk extracellular domain, the $LRM_3$-cassette and the Ig2-domain. Binding assays utilizing these expressed domains indicated that the $LRM_3$-cassette of TrkA and TrkB was capable of binding NGF and BDNF, NT-3 and NT-4, respectively, whereas the Ig2-domain bound none of the neurotrophins.

More detailed analysis of the structures within the $LRM_3$-cassette responsible for the binding of the individual neurotrophins resulted in a finding that a single, 24 amino acid single leucine-rich motif of TrkB, namely the second one ($LRM_2$), binds all three ligands, BDNF, NT-3 and NT-4 and that the corresponding $LRM_2$ of TrkA is responsible for binding this receptor's primary ligand, NGF.

Accordingly, the present invention is directed to the 24 amino acid leucine rich motif ($LRM_2$) in each of the Trk receptors TrkA, TrkB, and TrkC. With respect to the human Trk receptors, these $LRM_2$ domains comprise peptides having amino acid sequences as set forth below:

TRKA: T I V K S G L R F V A P D A F H F T P R L S R L (SEQ ID NO:1)

TRKB: T I V D S G L K F V A H K A F L K N S N L Q H I (SEQ ID NO:2)

TRKC: T I K N S G L R S I Q P R A F A K N P H L R Y I (SEQ ID NO:3)

The present invention further contemplates the corresponding $LRM_2$ of Trk receptors derived from other species. As used herein, the corresponding $LRM_2$ refers to the second leucine rich motif which is the functional equivalent of the $LRM_2$ described herein for the human Trk receptor; i.e. the $LRM_2$ binds to the same neurotrophin(s) as its human homolog. For example, the following peptides correspond to the second LRM in rat TrkA and TrkB:

TrkA: T I V K S G L R F V A P D A F H F T P R L S H L (SEQ ID NO: 4)

TrkB: T I V D S G L K F V A Y K A F L K N G N L R H I (SEQ ID NO: 5)

When used herein, $LRM_2$'s include peptides having the same sequence as found in the Trk receptor from which it is derived, as well as functionally equivalent molecules in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

The present invention further provides for isolated nucleic acid molecules encoding the $LRM_2$ of the Trks as described herein, as well as vectors comprising the isolated nucleic acid molecules, which can be used to express $LRM_2$'s in bacteria, yeast and mammalian cells. Accordingly, nucleic acid sequences encoding $LRM_2$'s include those having the following sequences:

a) nucleotide sequences encoding an $LRM_2$ having an amino acid sequence of T I V K S G L R F V A P D A F H F T P R L S R L (SEQ ID NO:1);

b) nucleotide sequences encoding an $LRM_2$ having an amino acid sequence of T I V K S G L R F V A P D A F H F T P R L S H L (SEQ ID NO: 4);

c) nucleotide sequences that hybridize under moderately stringent conditions to the nucleotide sequence of (a) or (b) and which encode an $LRM_2$ protein that binds a specific neurotrophin; and d) nucleotide sequences that are degenerate as a result of the genetic code to a nucleotide sequence of (a) or (b), and which encode an LRM$_2$ protein that binds a specific neurotrophin.

Accordingly, the invention provides for nucleic acids, or oligonucleotides greater than about 10 bases in length, that hybridize to the $LRM_2$ encoding nucleic acid described herein and remain stably bound to it under low to moderate stringency conditions. Conditions of moderate stringency, as used herein, include, for example, those conditions set forth in Sambrook, et al. Molecular Cloning: A Laboratory Manual, 2 ed. Vol. 1, pp. 101–104, Cold Spring Harbor Laboratory Press (1989).

The present invention further provides for use of the peptides described herein in screening for compounds that interact with the Trk receptors. Novel agents that bind to the peptide(s) described herein may mediate survival and differentiation in cells expressing the trk receptors, but may also act as antagonists to the trk receptors. In particular embodiments, the peptides described herein are utilized in screens for cognate ligands.

The peptide molecules useful for practicing the present invention may be prepared synthetically or may be prepared by cloning and expression in a prokaryotic or eukaryotic expression system. They may be expressed and purified utilizing any number of methods. The nucleic acid encoding the selected peptide may be subcloned into a bacterial expression vector, such as for example, but not by way of limitation, pCP110.

In particular embodiments of the invention, a $LRM_2$ is prepared as a fusion protein, dimer or in some other desirable polymeric form. Preferably, the $LRM_2$ is expressed as a fusion protein, dimer or polymer which includes an additional component that confers upon the molecule a desirable physiological and/or therapeutic property, such as enhanced half-life, solubility, biological compatibility, or enhanced conformation (which may prove useful for screening utilities).

In one embodiment, a $LRM_2$ is produced as a fusion protein, as described, for example, in the Materials and Methods section below, using the pMal™-p expression vector, which results in Maltose Binding Protein-$LRM_2$ fusion protein. In other embodiments, $LRM_2$s may be expressed as fusion proteins or engineered using known fusion regions, as described in published PCT application WO 93/10151 published May 27, 1993.

In another embodiment, chimeric homodimers are prepared using a similar method, but using the Fc-domain of human IgG1 [Aruffo et al., 1990, Cell 67:35–44; Shelton, et al. 1995, J. Neuroscience 15:477–491]. Using standard techniques, sequences encoding the leucine rich domains described herein are fused in frame with sequences encoding the Fc domain of human IgG heavy chain, resulting in secretion of molecules encoding two of the leucine rich domains linked via the Fc region (Ashkenazi et al, 1993, Intern. Rev. Immunol 10:219–227).

The $LRM_2$'s described herein have potential when utilized alone, or preferably in the form of biologically compatible chimeras, such as Fc chimeras, as therapeutics that block the biological effects of endogenous neurotrophins. For example, as described in Shelton, et al. 1995, J. Neuroscience 15:477–491, chimeras comprising the entire extracellular domain of TrkA, TrkB and TrkC fused by the Fc region of human IgG were potent inhibitors of the biological activity of NGF, BDNF and NT-3 biological activity, respectively.

A more immediate utility of the claimed $LRM_2$ molecules is their use in high throughput screening assays utilized for identifying both agonists and antagonists of the neurotrophins. Applicants have provided the first demonstration that a discrete region of the Trk receptors determines their ability to bind to specific neurotrophins. This discovery provides a powerful tool for use in assay systems that may be utilized to screen libraries of compounds that can bind, and therefore act as agonists or antagonists in these systems. Further, because the present invention provides for the production of $LRM_2$ dimers which may mimic the presentation of the Trk receptors in their natural cellular environment, they may be ideal in assay systems useful for identifying small molecules that act on the critical receptor components in a dimerized state.

For example, in one embodiment, antagonists of the TrkA receptor may be identified as test compounds that are capable of interfering with the interaction of the TrkA $LRM_2$ described herein and nerve growth factor (NGF). Such antagonists may be identified by their ability to block the binding of a biologically active NGF to the $LRM_2$, as measured, for example, using BIAcore.

Alternatively, the present invention provides for a method of identifying an agent that has the biological activity of a neurotrophin comprising (i) exposing a $LRM_2$ to a test agent and (ii) detecting the specific binding of the test agent to the $LRM_2$, in which specific binding to the $LRM_2$ positively correlates with neurotrophin like activity. The term "neurotrophin-like activity," as used herein, should be construed to refer to the activity of NGF, BDNF, NT-3, or NT-4 or any other, hitherto unidentified neurotrophin. Agents that exhibit neurotrophin activity include but are not limited to neurotrophic and non-neurotrophic factors, including peptide and non-peptide molecules, that have biological activity similar to the neurotrophins with respect to immediate early gene induction, cell types affected, phenomena induced, etc. Biological activities of BDNF and NT-3 are described, respectively, in PCT application numbers PCT/US90/04915 and PCT/US90/04916; NT-4 biological activies are described in Ip, et al. 1992 Proc. Natl. Acad. Sci. U.S.A. 89:3060–3064; NGF activity is described in Thoenen and Barde, 1980, Physiol. Rev. 60:534–569, which are incorporated by reference in their entirety herein.

The above method may be particularly useful in identifying new members of the neurotrophin ligand family or, in the pharmaceutical industry, in screening a large array of peptide and non-peptide agents (e.g., peptidomimetics) for neurotrophin like biological activity.

In a preferred, specific, nonlimiting embodiment of the invention, a large grid of culture wells may be prepared that contain, in alternate rows, $LRM_2$-Fc dimers. A variety of test agents may then be added such that each column of the grid, or a portion thereof, contains a different test agent. Each well could then be scored for the presence or absence of binding to the $LRM_2$-Fc dimer. An extremely large number of test agents could be screened for such activity in this manner.

EXAMPLE 1

MATERIALS AND METHODS

Neurotrophins. Recombinant *E. coli*/vaccinia virus expressed mouse BDNF, mouse NT-3 (Gotz et al., 1992, Nature 372:266–269), and Xenopus NT-4 were kind gifts of R. Kolbeck, G. Dechant and Y.-A. Barde. Mouse submaxillary gland NGF-β, was purchased from Sigma Immuno Chemicals. $^{125}$I-BDNF, $^{125}$I-NT-3 and $^{125}$I-NT-4 were prepared using the lactoperoxidase method, $^{125}$I-NGFβ was purchased from Amersham.

Cloning and Expression of Receptor Modules. The regions coding for the different Trk A and TrkB modules were amplified from rat brain mRNA by RT-PCR and cloned into the pMal™-p expression vector. The sequences of the fragments were identical to the ones published in the literature (Meakin, et al. 1992, Proc. Natl. Acad. Sci. U.S.A. 89:2374–2378; Klein, et al. 1989. EMBO J. 8:3701–3709). The recombinant Maltose Binding Protein (MBP)-TrkA/B fusion proteins were expressed in *E. coli* and purified essentially as described in the manufacturer's protocol (New England Biolabs 1990). For the negative controls a fusion protein composed of MBP and β-Galactosidase (MBP-βGal) was expressed. The purified proteins were extensively dialyzed against 20 mM Tris-Cl pH 7.4, 200 mM NaCl, 1 mM EDTA (column buffer) before using them in the experiments.

Qualitative binding assays. 500 ng of recombinant protein/assay were batch loaded onto 5 μl of amylose resin in 25 μl of column buffer. After centrifuging, the supernatants were removed and the pellets washed three times with column buffer. In order to minimize non-specific binding, the column material was pretreated by resuspending in 90 μl column buffer+5 mg/ml BSA+0.1 mg/ml Cytochrome c (bovine heart)+2 mg/ml heat denatured BSA+0.1 mg/ml heat denatured Cytochrome c and incubated with gentle shaking for 30 min. The denatured proteins were included to give a more solid amylose resin pellet after centrifugation 5 μl of $^{125}$I-BDNF, $^{125}$I-NT-3, $^{125}$I-NT-4, or $^{125}$I-NGF at $4 \times 10^{-9}$M were added and incubated with gentle shaking at 20° C. for 90 min to reach equilibrium binding. Each binding reaction was carried out in duplicate and for each concentration of $^{125}$I-Neurotrophin, a MBP-βGal control was made to detect non-specific binding to MBP. After centrifuging for 3 min the supernatants were transferred to fresh tubes (SN1). The pellets were washed three times in column buffer containing 20 mM maltose to elute the receptor-ligand complexes. The supernatants of all three centrifugation steps were combined in a new tube (SN2). SN1, SN2 and the amylose resin pellet were measured on a gamma counter. SN1 therefore represented free $^{125}$I-Neurotrophin, SN2 specifically bound $^{125}$I-Neurotrophin. The small amounts of radioactivity trapped in the pellet were added to the free $^{125}$I-Neurotrophin. Non-specific binding to the MBP in the control experiments was low and subtracted from the specific binding in each case.

Equilibrium Binding Assays. Binding reactions of 100 μl final volume containing 1.25 pmol (100 to 200 ng, depending on the Mr) of recombinant protein/assay were prepared as described above. Final concentrations of $^{125}$I-BDNF or $^{125}$I-NT-3 ranged from $7.8125 \times 10^{-12}$M to $4 \times 10^{31}$ $^9$M. The samples were processed as described above. All data points are means of duplicates. The data are corrected for non-specific binding.

All calculations were performed according to Bylund and Yamamura 1990 in Methods in neurotransmitter receptor analysis, Yamaura, et al, Eds., pp 1–35, Raven Press, New York and Unnerstall 1990 Methods in neurotransmitter receptor analysis, id, pp37–78, Raven Press, New York using the GraFit program (Erithacus).

RESULTS AND DISCUSSION

To identify the contributions the individual structural entities within the extracellular domains of the Trk receptors make to the process of binding the neurotrophins, these modules were expressed in recombinant soluble form as described above and tested for their ability to bind the individual ligands. To do so, the recombinant proteins were immobilized on amylose resin column matrices and binding of the iodinated neurotrophins to the individual receptor molecules were assessed using quantitative binding assays. Table 1 sets forth the results obtained in equilibrium assays utilizing the entire extracellular domain of TrkA and TrkB, as well as expressed versions of specific domains from these receptors. The values in Table 1 are equilibrium binding constants ($K_d$s) in nM units. A "+" indicates binding of the neurotrophin in a qualitative binding assay using receptor affinity columns (no $K_d$ determined). A "−" indicates that no binding of the neurotrophin to the respective receptor module could be detected, n.d. that no value was determined. Abbreviations: C I, C II: cysteine clusters I and II; LRM: leucine-rich motif; TH:transmembrane helix; TK:tyrosine kinase; Ex:extracellular domain (TrkA: Cys36-Glu416; TrkB: Cys21-Glu417); $LRM_3$: $LRM_3$-cassette (TrkA:Cys36-Pro196; TrkB: Cys 21-Pro 186); Ig:Ig2-domain (TrkA; Ser197-Glu416; TrkB: Ser 187-Glu417); $L_{1-3}$: $LRM_3$-cassette lacking both cysteine clusters (TrkA:Tyr7-Leu143); $L_{2-3}C_2$:$LRM_3$-cassette lacking the first cysteine cluster and the first LRM (TrkA:Thr97-Pro196); $C_1L_{1-2}$: $LRM_3$-cassette lacking the third LRM and the second cysteine cluster (TrkA: Cys36-Leu120); $C_1L_{1-1.5}$: $LRM_3$-cassette lacking the C-terminal half of the second LRM, the third LRM and the second cysteine cluster (TrkA: Cys36-Pro108); $L_{1.5-3}C_2$: $LRM_3$-cassette lacking the first cysteine cluster, the first LRM and the first half of the second LRM (TrkA: Asp109-Pro196); L2:the isolated 24 amino acid second leucine-rich motif (TrkA: Thr97-Leu120). The numbers indicating the boundaries of the expressed domains are stated according to Meakin, et al. 1992 Proc. Natl. Acad. Sci. U.S.A. 89:2374–2378for TrkA and according to Middlemas et al. 1991 Mol. Cell. Biol. 11:143–153 for TrkB.

Similarly Table 2 sets forth the results obtained from additional experiments utilized to determine the specific binding site of BDNF, NT-3 and NT-4 on TrkB. All Kd values are in $10^{31}$ $^9$M. The abbreviations in this table are as follows: TrkB: Ex: entire extracellular domain (C21-E417); $LRM_3$:$LRM_3$-cassette (C21-P186); Ig2: Ig2-domain (S187-E417); LI-3: $LRM_3$-cassette lacking both cysteine clusters (L61-L132), L2: isolated second LRM (T86-L109); the residue numbers here are stated according to Middlemas et al. 1991 Mol. Cell. Biol. 11:143–153; TrkA: Ex:C36-E416 (according to Meakin, et al. 1992 Proc. Natl. Acad. Sci. U.S.A. 89:2374–2378); +neurotrophin binding; −no neurotrophin binding detectible.

Immobilized on a column, the entire extracellular domains of Trk and TrkB were found to exhibit the same ligand binding specificities that have been previously described, i.e. NGF bound to trkA, and BDNF and NT-3 bound to TrkB.

Subsequent analysis, utilizing recombinant Ig2-domain revealed that this domain had no detectable affinity to NGF, BDNF or NT-3, thus suggesting a role of the $LRM_3$ domain as the major neurotrophin binding site. This structural entity of TrkA as well as TrkB could still discriminate specifically between NGF, BDNF and NT-3 identifying it as the ligand binding site containing region.

TrkA was used to systematically identify the exact location of a neurotrophin binding site. Creating appropriate expression vector constructs, the two cysteine clusters flanking the $LRM_3$-cassette were removed first ($L_{1-3}$) followed by elimination of the first ($L_{2-3}$ $C_2$) and the third ($C_1L_{1-2}$) LRM repeat in two separate approaches. All of these recombinant receptor proteins showed the same namomolar affinities and specificities for their respective neurotrophins suggesting that the 24 amino acids of the middle LRM are sufficient to constitute an NGF binding site (Table 1). Similarly, more detailed analysis of the structures within the $LRM_3$ cassette of TrkB responsible for the binding of the individual neurotrophins BDNF, NT-3 and NT-4 yielded surprising results (TABLE 2). Surprising, a 24 amino acid single leucine-rich motif of TrkB namely, the second one (L2) was found to bind to all three ligands, BDNF, NT-3 and NT-4. Further data (not shown) indicated similar results utilizing the $LRM_2$ of TrkC (SEQ ID NO: 3), which was found to bind neurotrophin-4.

The second LRM of rat TrkB shares 13 identical amino acids with the second LRM of rat TrkA, leaving eleven amino acid residues to account for the specificity of binding three different neurotrophins. This firmly establishes the second leucine-rich motif ($LRM_2$) as one of the most potent and flexible protein-protein interaction motifs.

An examination of the binding affinities of the receptor complex in vivo, as determined by the equilibrium binding constants (Kds) of the interactions of $^{125}$I-BDNF, $^{125}$I-NT-3 and $^{125}$I-NT-4 with the second LRM (L2) as well as with the $LRM_3$-cassette and the entire extracellular domain (Ex) of TrkB (Table 2) indicates that the differences in the affinities of Ex, $LRM_3$ and $L_2$ for each of the ligands $^{125}$I-BDNF, $^{125}$I-NT-3 and $^{1251}$I-NT-4 were minimal. This indicates that we have indeed mapped the only binding site present in the receptor in this conformational stage. The affinities of $L_2$ for BDNF and NT-3 are very similar with Kds of approximately 1 nM as determined by steady state binding. These values are in good agreement with the ones obtained in experiments with cells ectopically expressing TrkB receptors. Soppet et al. 1991, Cell 65:895–903 found that mouse NIH 3T3 fibroblasts expressing rat TrkB bind $^{125}$I-BDNF with a Kd of about $1.8 \times 10^{-9}$M and $^{125}$I-NT $_{-3}$ with a Kd of about $1.3 \times 10^{-9}$M. Dechant et al. 1993 Development 119:545–558 determined a very similar value for $^{125}$I-BDNF binding to chick TrkB ectopically expressed in the human embryonic kidney cell line A293. This indicates that $L_2$ represents a binding site that is of quantitative importance within the TrkB receptor. However, it does not display the high-affinity binding component (Kd of about $1.7 \times 10^{-11}$M) exhibited by embryonic chick dorsal root ganglia (Rodriguez-Tebar & Barde, 1988, J. Neuroscience 8:3337–3342; Rodriguez-Tebar et al., 1992, EMBO J. 11:917–922), sympathetic (Rodriguez-Tebar et al., 1993 Eur. J. Biochem. 211:789–794) or other neurons.

A possible explanation for this phenomenon is that in the proper cellular environment the neurotrophin could be transferred from $L_2$ to a high-affinity binding site within the Trk receptor formed by a conformational change upon ligand binding. High-affinity binding may also require the action of additional receptor components (membrane proteins or extracellular matrix components such as proteoglycans, as has recently been shown for NT-6 (Gotz et al., 1994, Nature 372:266–269) which might only be present or present in the correct stoichiometric relations in such neurons. Other researchers have suggested that intact signal transduction pathways may be required for the generation of high-affinity binding sites (Raffioni et al., 1993, Annu. Rev. Biochem. 62:823–850). $p75^{LNTR}$ has been discussed as an possible factor that could turn on these pathways possibly leading to some post-translational modification of Trk receptors or to the association with other receptor components (Meakin & Shooter, 1992 Trends Neurosci. 15:323–331).

An interesting possibility arising from our results is that the promiscuity observed in Trk-type receptors might be based on the allocation of the binding sites for the different neurotrophins to distinct LRMs within the $LRM_3$-cassette. This would, for example, allow a BDNF and an NT-3 molecule to simultaneously bind to one and the same TrkB receptor.

Nonetheless, applicants have described, for the first time, a peptide region the Trk receptors that is associated with binding to the neurotrophin family of neurotrophic factors. This region provides a powerful tool to assay for neurotrophin agonists or antagonists whose site of action is in this critical region.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

TABLE 1

| Domain | Neurotrophin binding affinity ($K_d$) | | |
|---|---|---|---|
| | NGF | BDNF | NT-3 |
| Trk A Ex | 1.29 ± 0.20 | – | – |
| TrkB Ex | – | 0.93 ± 0.17 | + |
| TrkA $C_1L_{1-3}C_2$ | 1.09 ± 0.24 | – | – |
| TrkB $C_1L_{1-3}C_2$ | – | 1.16 ± 0.23 | + |
| TrkA Ig | – | – | – |
| TrkB Ig | – | – | – |
| TrkA $L_{1-3}$ | 0.97 ± 0.22 | – | – |
| TrkA $L_{2-3}C_2$ | 1.15 ± 0.25 | – | n.d. |
| TrkA $C_1L_{1-2}$ | 0.84 ± 0.30 | – | n.d. |
| TrkA $C_1L_{1-1.5}$ | – | – | n.d. |
| TrkA $L_{1.5-3}C_2$ | – | – | n.d. |
| TrkA $L_2$ | 1.33 ± 0.36 | – | – |

TABLE 2

| | Module | $^{125}$I-Neurotrophin | | | |
|---|---|---|---|---|---|
| | | BDNF | NT-3 | NT4 | NGF |
| TrkB | Ex | 0.93 ± 0.17 | 1.32 ± 0.33 | + | – |
| | $LRM_3$ | 1.16 ± 0.23 | 1.43 ± 0.29 | + | – |
| | Ig2 | – | – | – | – |
| | $L_{1-3}$ | + | + | + | – |
| | $L_2$ | 1.39 ± 0.21 | 1.17 ± 0.43 | + | – |
| TrkA | Ex | – | – | – | 1.29 ± 0.20 |

We claim:

1. Isolated and purified leucine rich motif (LRM$_2$) of the TrkA receptor having a sequence selected from the group consisting of the following sequences:
   a) T I V K S G L R F V A P D A F H F T P R L S R L (SEQ ID NO:1); and
   b) T I V K S G L R F V A P D A F H F T P R L S H L (SEQ ID. NO: 4).

2. Isolated and purified leucine rich motif (LRM$_2$) of the TrkB receptor having a sequence selected from the group consisting of the following sequences:
   a) T I V D S G L K F V A H K A F L K N S N L Q H I (SEQ ID NO:2); and
   b) T I V D S G L K F V A Y K A F L K N G N L R H I (SEQ ID NO: 5).

3. Isolated and purified leucine rich motif (LRM$_2$) of the TrkC receptor having the following sequence:
   a) T I K N S G L R S I Q P R A F A K N P H L R Y I (SEQ ID NO:3).

4. An isolated and purified nucleic acid encoding an LRM$_2$ according to claim 1.

5. An isolated and purified nucleic acid encoding an LRM$_2$ according to claim 2.

6. An isolated and purified nucleic acid encoding an LRM$_2$ according to claim 3.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:1:

```
Thr  Ile  Val  Lys  Ser  Gly  Leu  Arg  Phe  Val  Ala  Pro  Asp  Ala  Phe  His
1                   5                        10                           15

Phe  Thr  Pro  Arg  Leu  Ser  Arg  Leu
                    20
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:2:

```
Thr  Ile  Val  Asp  Ser  Gly  Leu  Lys  Phe  Val  Ala  His  Lys  Ala  Phe  Leu
1                   5                        10                           15

Lys  Asn  Ser  Asn  Leu  Gln  His  Ile
                    20
```

( 2 ) INFORMATION FOR SEQ ID NO:3:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:3:

```
Thr  Ile  Lys  Asn  Ser  Gly  Leu  Arg  Ser  Ile  Gln  Pro  Arg  Ala  Phe  Ala
1                   5                        10                           15

Lys  Asn  Pro  His  Leu  Arg  Tyr  Ile
                    20
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:4:

```
Thr  Ile  Val  Lys  Ser  Gly  Leu  Arg  Phe  Val  Ala  Pro  Asp  Ala  Phe  His
1                   5                        10                           15
```

Phe Thr Pro Arg Leu Ser His Leu
20

( 2 ) INFORMATION FOR SEQ ID NO:5:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: unknown ( i i ) MOLECULE TYPE: peptide ( x i ) SEQUENCE DESCRIPTION: SEQ ID NO:5:

Thr Ile Val Asp Ser Gly Leu Lys Phe Val Ala Tyr Lys Ala Phe Leu
1               5                       10                      15

Lys Asn Gly Asn Leu Arg His Ile
20